United States Patent [19]
Wedegaertner et al.

[11] Patent Number: 5,750,466
[45] Date of Patent: May 12, 1998

[54] COATED COTTONSEED AND A PROCESS FOR ITS MANUFACTURE

[75] Inventors: Thomas C. Wedegaertner; Thomas D. Valco; William F. Lalor, all of Raleigh, N.C.

[73] Assignee: Cotton Incorporated, New York, N.Y.

[21] Appl. No.: 691,578

[22] Filed: Aug. 2, 1996

[51] Int. Cl.⁶ .............. A01N 25/26; A23K 1/14; A23K 1/16; A01C 1/06
[52] U.S. Cl. .............. 504/100; 47/57.6; 47/DIG. 9; 426/630
[58] Field of Search .............. 504/100; 47/57.6, 47/DIG. 9; 426/630

[56] References Cited

U.S. PATENT DOCUMENTS

| | | | |
|---|---|---|---|
| 2,166,974 | 7/1939 | Shields | 19/66 |
| 2,240,503 | 5/1941 | Kettenbach | 83/27 |
| 2,302,526 | 11/1942 | Card | 99/235 |
| 2,502,809 | 4/1950 | Vogelsang | 47/58 |
| 2,579,732 | 12/1951 | Funsten et al. | 47/1 |
| 2,656,649 | 10/1953 | Oster | 47/1 |
| 3,808,740 | 5/1974 | Porter et al. | 47/58 |
| 3,911,183 | 10/1975 | Hinkes | 428/15 |
| 3,943,604 | 3/1976 | Harrington et al. | 19/43 |
| 3,991,517 | 11/1976 | Lewis | 47/57.6 |
| 4,259,764 | 4/1981 | Downing | 19/41 |
| 4,696,824 | 9/1987 | Meczkowski et al. | 426/102 |
| 5,204,102 | 4/1993 | Coles et al. | 424/195.1 |
| 5,361,457 | 11/1994 | Gordo et al. | 19/41 |
| 5,363,754 | 11/1994 | Coles et al. | 99/484 |
| 5,397,581 | 3/1995 | Lerman | 426/231 |
| 5,423,107 | 6/1995 | Thrash | 19/40 |
| 5,471,971 | 12/1995 | Hsu | 99/536 |

OTHER PUBLICATIONS

*Textile Slashing Short Course*, Proceedings, The Department of Textile Engineering, Auburn University, Auburn, Alabama (1986).

*Textile Slashing Short Course*, Proceedings, The Department of Textile Engineering, Auburn University, Auburn, Alabama (1984).

*Theory and Practice of Textile Slashing*, First edition., Monograph No. 1, Auburn University, Auburn, Alabama (1972).

Primary Examiner—S. Mark Clardy
Attorney, Agent, or Firm—Burns, Doane, Swecker & Mathis, L.L.P.

[57] ABSTRACT

Linter-bearing cottonseed covered with a coat of starch optionally containing one or more biologically related materials selected from vitamins, feed supplements, oils, fats, urea, rodent repellants, insect repellants, medications, antigermination agents, and preservatives, and a method for preparing it is taught herein. Starch coated cottonseed is useful as an animal feed and as planting stock. The starch coating allows the cottonseed to be used in conventional feed handling and seed planting equipment.

13 Claims, 3 Drawing Sheets

COATED COTTONSEED AND A PROCESS FOR ITS MANUFACTURE

FIELD OF THE INVENTION

The present invention relates to linter-bearing cottonseed, covered with a coating of starch to adapt it for use with animal feed handing equipment currently used on farms and ranches, and a process for applying the coating to the cottonseed.

BACKGROUND OF THE INVENTION

Cottonseed is rich in nutrients and is highly regarded by dairy cattle producers as a favored feed stock for their herds. Cottonseed would be even more popular as a feed if it could be shipped, stored and distributed by conventional feed handling equipment. After the cotton has been picked from the boll of the cotton plant, it is processed through a gin which combs through the cotton to separate the seeds from the cotton fibers. The cottonseed as it comes from the gin is covered with a thin coat of residual cotton fibers, known as "linters," or "fuzz" giving the cottonseed a fuzzy appearance. The protruding linters on each seed have a strong tendency to interlock with the linters of neighboring seeds, causing the seeds to stick together rather than flow. The poor ability of cottonseed to flow creates the need for specialized equipment to handle and transport cottonseed.

The cotton gin and the textile producing machinery of the late industrial revolution lead to a dramatic increase of cotton production and, consequently, a corresponding increase in cottonseed. Initially cottonseed was considered a waste byproduct of little commercial value except for planting to produce the next season's crop. Circa the middle of the nineteenth century, it was discovered that cottonseed could be squeezed to yield a useful oil. Later the residue of the oil making process was used as a-feed supplement for grazing animals. In recent years the demand for whole cottonseed as feed for livestock has significantly increased.

Because planting was a labor intense, by-hand-process and cottonseed oil production used specialized machinery designed for that purpose, the tendency of cottonseed to clump together was not viewed as much of a problem in the nineteenth century. However, the advent of highly mechanized agriculture in the first half of this century and the increase in demand for whole cottonseed as a livestock feed, have raised concern about the difficulty of handling cottonseed.

The livestock feed industry's requirements for cottonseed are different from the requirements of the planting seed industry. For example, relatively speaking, planting seed is characterized by high quality, high cost, and low volume. By comparison, cottonseed for use as a feed is characterized by lessor quality, low to moderate cost, and high volume. Therefore, a high cost per unit volume for improving the flow characteristics of planting seed may be acceptable whereas it would not be for livestock feed. As a further example, heating during processing may affect the germination of planting seed, whereas, moderate heating or roasting of feed stock seed may actually improve its feed value for cattle.

Most of the processes of the art for improving the flow characteristic of cottonseed involve removal of the linters by mechanical means, chemical means or by singeing. Coles, et al. in U.S. Pat. Nos. 5,204,102 and 5,363,754, teach coated cottonseed for use as animal feed and the apparatus to produce it. Specifically, Coles et al. teach delinting the cottonseed by singeing before coating and the use of a sticky "binder" to hold a "filler" on the cottonseed. The "binder" of Coles et al. is selected from molasses, gum, starch or lignasite, and the "filler" is an inorganic mineral powder or textured protein.

Any such removal of linters requires an additional process step that results in extra cost for equipment, materials, and energy. Further, the linters have some nutritional value for ruminant animals, so where cottonseed is to be used as feed, retaining the linters is beneficial.

It is an object of the present invention to provide coated, linter-bearing cottonseed for particular use as an animal feed with flow characteristics that allow it to be handled and transported by conventional equipment. It is also an object to provide a process for preparing such coated cottonseed on which the linters have been retained, i.e., without delinting.

SUMMARY OF THE INVENTION

The first aspect of the present invention is linter-bearing cottonseed covered with a coat of starch, optionally containing vitamins, feed supplements, oils, fats, urea, anti-fungal agents, rodent repellants, insect repellants, medications, anti-germination agents and preservatives.

As a feed stock for animals, the coated cottonseed, of this invention, is particularly useful because it can be handled and transported by conventional feed and grain handling and transporting equipment widely available to farmers, dairymen, and ranchers. Further, optional ingredients in the coating may enhance the nutritional value of the cottonseed, prolong its storage life, and increase the durability of the coating.

The second aspect of the present invention is a process for coating cottonseed consisting essentially of the steps of:

a) spraying linter-bearing cottonseed with a coating consisting essentially of a hot, aqueous, gelatinized starch suspension, optionally containing one or more biologically related materials selected from vitamins, feed supplements, oils, fats, urea, anti-fungal agents, rodent repellants, insect repellants, medications, anti-germination agents, and preservatives, while agitating said linter-bearing cottonseed to yield starch suspension coated cottonseed;

b) drying said starch suspension coated cottonseed to yield starch coated cottonseed;

c) disaggregating said starch coated cottonseed; and d) cooling and storing said starch coated cottonseed.

Steps a, b, and c may be repeated one or more times to provide a double or multiple coating. Optionally, the coated cottonseed may be roasted and heat-steeped.

DETAILED DESCRIPTION OF THE PREFERRED EMBODIMENT

As used herein, terms "cotton seed," "seed of cotton," and "seed" can be singular or plural and refer to the individual components of the commodity referred to by the singular, collective term "cottonseed".

Figure 1:
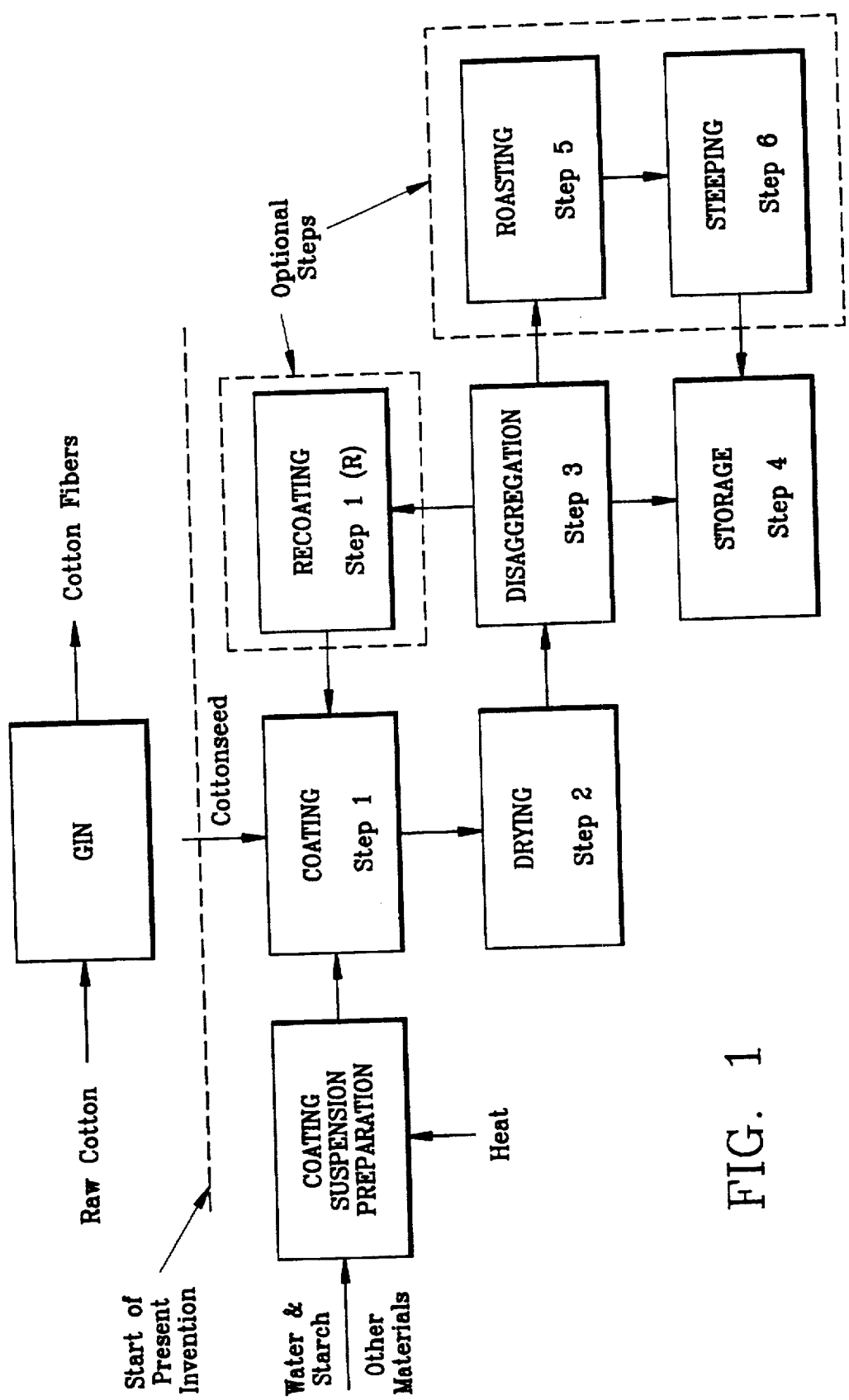
FIG. 1 is a flow chart illustrating the steps of the process of the present invention for preparing coated cottonseed.

Referring to the flow chart of FIG. 1, before the start of the present process, cottonseed is removed from the raw cotton, i.e., as it comes from the boll of the cotton plant, in the ginning operation. The deseeded cotton is further processed into fabric. Preferably, the cottonseed used as the starting material in the present process has previously had most of the longer fibers removed.

In Step 1 of the coating process shown in FIG. 1 the linter-bearing cottonseed is sprayed with a hot, gelatinous starch suspension with agitation to uniformly coat the cottonseed with the gelatinous starch suspension. The thickness of the coating is a function of three major factors: a) the viscosity of the starch suspension, b) the concentration of starch, and c) the time the seeds are being sprayed with the suspension. Each of these factors can be varied to adjust the thickness of the coating.

The gelatinous starch suspension may be prepared in a starch cooking vessel equipped with means for heating and stirring the suspension. It is known in the art of preparing starch suspensions, e.g., see *Theory and Practice of Textile Slashing*, 1st Ed., Monograph No.1, Auburn University, Auburn, Ala. (1972), that the starch and water should be mixed in a certain range of proportions, in a certain sequence, and in a certain temperature range to obtain a smooth and uniform gelatinous suspension. The starch suspension preferred for the process of the present invention is about 2% to about 25% starch by weight, and is heated at a temperature from about 76° C. to boiling with stirring until it is gelatinized. It will be appreciated by those skilled in the art that a gelatious starch suspension can be prepared by a batch or continuous process.

Starch from a variety of sources may be used for the present invention. For example, potato, wheat, and corn starches or mixtures thereof are acceptable. Therefore, the choice of starch depends on its availability as well as economic considerations.

The essential ingredients of the gelatinous starch suspension are starch and water, but one or more optional biologically related ingredients such as vitamins, food supplements, oils, fats, urea, anti-fungal agents, rodent repellants, insect repellants, medications, anti-germination agents, and preservatives may be added to enhance the properties of the coated cottonseed. For example, a coating might contain a vitamin mixture plus a coloring agent to identify easily the enhanced coated cottonseed. Further, small quantities of surfactants, e.g., wetting agents, may be added to the starch suspension to promote uniform coating. The optional ingredients can be added anytime during the starch suspension preparation, but conveniently may be added near the end of the cooking process, just before spraying on the cottonseed, or during agitation of the sprayed cottonseed.

In Step 2 the starch coated cottonseed is substantially dried by hot forced air. Conveniently this can be carried out by passing a stream of hot air (about 100° C. to about 150° C.) over and/or through a bed of coated seeds as they are moved by a means of conveying, such as a moving belt, grid or screen, through a drying chamber. The rate of drying can be controlled by the temperature of the stream of hot air, the rate of flow of the stream of hot air, and rate of movement of the seeds. These factors may be adjusted so that coating of the cottonseed as it leaves the drying chamber is hard but not brittle or flaky. Preferably, the coating should be dried so that the moisture level is between about 7% and about 11%.

In Step 3 clumps of coated seeds are broken up, i.e., disaggregated, by passing the coated cottonseed through a series of beaters. The disaggregation may be a single or multi-step process and may be consecutive or concurrent with Step 2. The beaters may be of any configuration known in the art for disaggregation of coated items, such as counter rotating drums with spikes projecting from the drums that pull the aggregated coated seeds apart. Alternatively, a series of beaters may be placed in the drying chamber taught in Step 2.

In. Step 4. The coated seeds are allowed to cool to ambient temperature, then placed in storage until packaged or shipped in bulk to the user. The stored coated cottonseed must be kept dry and protected from temperature extremes.

Step 1(R) is a recycling step. If a thicker coat is wanted, or if multiple coats are required, Steps 1, 2, and 3 may be repeated, i.e., the process may be recycled one or more times. (The broken line box in FIG. 1 indicates that step 1(R) is optional.) Applying multiple, thin coatings rather than a single, thick coating may be advantageous for some applications. Multiple, thin applications yield a hard starch coat that can withstand rough handling and long storage. Multiple, thin coatings are preferred for coated cottonseed to be used as planting stock. However, the application of a single, thick coat consumes less resources and energy to apply than multiple coats and is acceptable for many animal feed applications.

For most uses as a feed the degree of coating is preferably between about 5% and about 10% of the weight of the coated cottonseed (on the basis of dry starch and dry cottonseed). However, some specialized applications may require very thin or extra thick coatings, such as when several optional ingredients are included in the coating.

Starch from a variety of sources may be used for the present invention. For example, potato, wheat, and corn starches or mixtures thereof are acceptable. Therefore, the choice of the type of starch is based on availability and economic considerations.

The coated cottonseed prepared by Steps 1 through 4 also may be used as planting stock, i.e., seed planted to produce a crop for another growing season. Where the coated cottonseed is to be used as planting stock, multiple, thin coating is preferred to give the cottonseed a composite coat that is sufficiently durable to be used in mechanized planting equipment. The degree of coating is the same for planting stock as for feed stock. Further, when the intended use of the coated cottonseed is planting stock, the optional ingredients in the starch coating of the cottonseed may be antifungal agents, rodent repellants, germinating promoting agents, and preservatives, but would not be anti-germinating agents or other ingredients only useful for animal feed and detrimental to cotton plants.

Optionally, In step 5 (indicated as optional in FIG. 1 by the broken line box), the coated seeds may be further heated, preferably between about 140° C. and about 150° C. for about 5 min to about 15 min, to more completely remove residual moisture and to roast the coated cottonseed. In Step 6 (optional), the hot, dry coated cottonseed from Step 5 is allowed to steep in a holding area preferably at a temperature between about 100° C. and about 150° C. for about 20 min to about 30 min before the coated cottonseed is allowed to cool to ambient temperature and is put into long term storage, Step 4. The moisture content of the coated cottonseed after being subjected to Steps 5 and 6 preferably is between about 1% and about 5%.

The combination of roasting and steeping significantly lowers the moisture level within the seeds and reduces the level of microorganisms that can cause the seeds to spoil; thus, enabling the coated cottonseed to be stored for a long period. However, if the coated cottonseed is to be used within a few months of preparation, and is stored under dry, mild temperature conditions, these two extra steps are generally not needed. Roasting and steeping may also produce a richer feed stock for dairy cattle. However, the marginal increase in nutritional value must be balanced against the resources consumed in these two extra steps.

EXAMPLES

Figure 2:
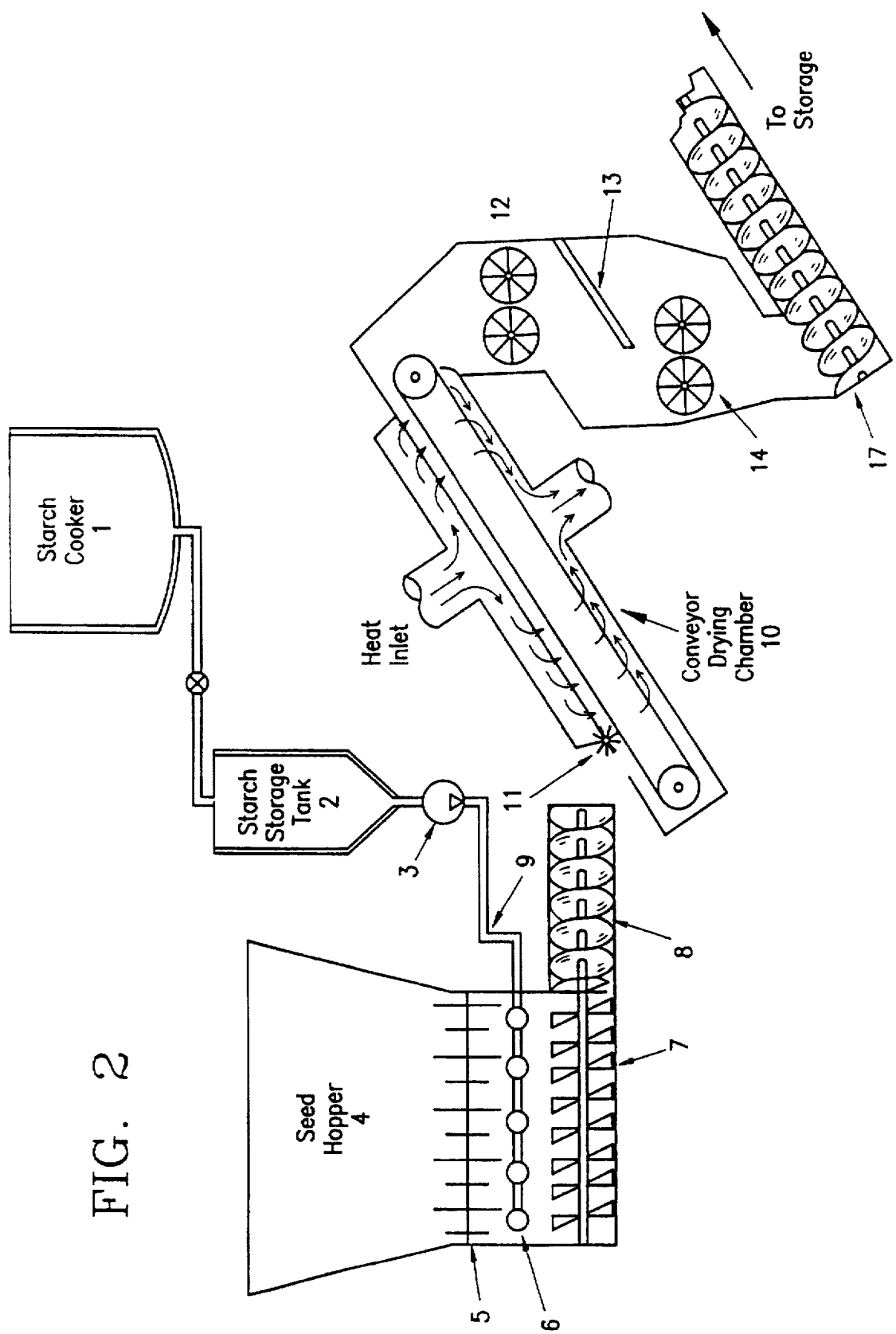
FIG. 2 is a schematic diagram related to the process of the present invention for preparing coated cottonseed to illustrate Examples 1, 2, and 3.
Figure 3:
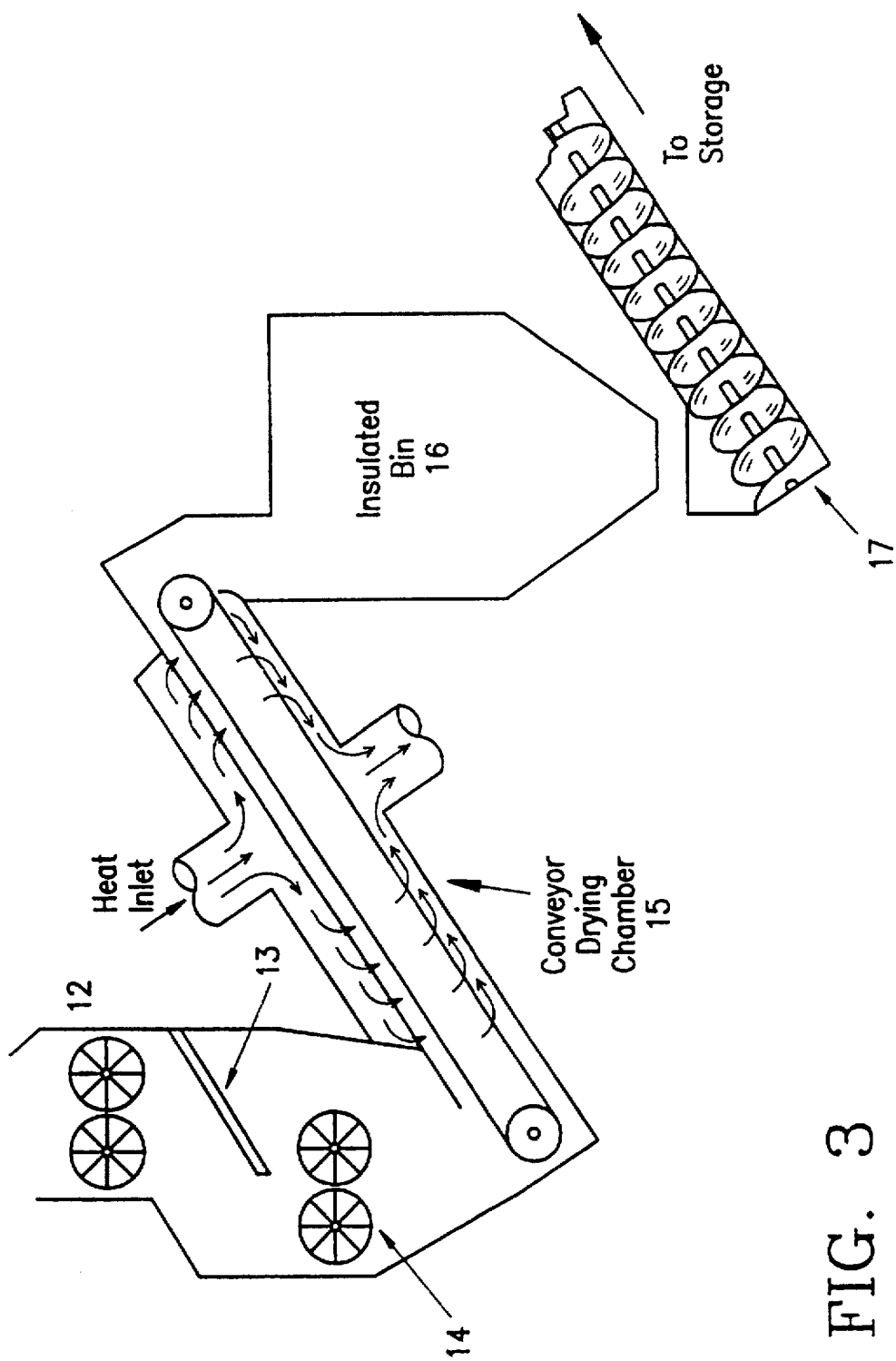
FIG. 3 is a schematic diagram related to the process of the present invention for preparing coated cottonseed to illustrate Example 4.

The following examples illustrate the present invention, but should not be construed as limitations thereof. FIG. 2 and FIG. 3 are schematic diagrams relating to the process taught above and illustrated by the flow chart of in FIG. 1, and are presented as aids in understanding these examples.

EXAMPLE 1

Preparation of 1000 Kg Batch of Coated Cottonseed

Referring to FIG. 2, a hot, gelatinous starch suspension is prepared by adding starch (64 Kg) and cool water (450 L) into a starch cooker 1 equipped with a stirrer and a steam jacket for heating. The starch and water are vigorously stirred to form a milk-like suspension that is then heated at, or near, boiling with stirring until the starch becomes gelatinous. That is, the milk-like suspension becomes a thick, translucent gel. The hot, gelatinous suspension is then pumped from the cooker through insulated piping into an insulated storage tank 2, where it is stored before coating the cottonseed.

Linter-bearing cottonseed in batches of about 250 Kg is charged into a seed hopper 4 from which it is moved by a series of metering wheels 5, into a mixing chamber above which is a series of spraying nozzles 6. As the hopper is depleted, more cottonseed is added until all of the 1000 kg has been placed in the hopper. The hot, gelatinous starch suspension, fed from the storage tank 2 is forced by a pump 3 through an insulated line out through the spraying nozzles 6 onto the cottonseed that is being agitated in the mixing chamber by a mixing auger 7. The gelatinous starch suspension is added at a rate so that the entire batch is applied uniformly to the 1000 Kg of cottonseed. (This rate of application may be determined by calculation considering the flow rate of the cottonseed and suspension or empirically using pilot batches.) As the mixing auger moves the cottonseed with random rotation through the mixing chamber, the cottonseed is sprayed from above by the spraying nozzles 6. The seeds are also rolled in the suspension collected in the bottom of the mixing chamber.

The coated cottonseed is moved out of the mixing chamber by the motion of the mixing auger and transferred by a screw auger 8 into a conveyor drying chamber 10 and onto a ventilated conveyor belt. As the coated seeds enter the drying chamber on the conveyor belt, they pass under a leveling wheel 11, which is set just high enough above the conveyor belt to produce a uniform bed depth of about 1.5 cm thick. During the approximate 5 min the coated seeds are transient in the drying chamber, forced hot air (about 110° C. to about 125° C.) is passed over and through the bed of coated seeds.

During the coating and drying process the coated seeds tend to aggregate together. As the coated seed leave the drying chamber on the conveyor belt they are allowed to fall through the disaggregation chamber where they pass through a first set of beaters 12, i.e., a pair of counter rotating drums with spike extensions, which breaks up most of the aggregates. The coated seeds then drop onto a sloping, sorter screen 13 having a mesh sized so that single coated seeds pass through while coated seeds that are still aggregated slide across the top of the screen. The remaining aggregated seeds then fall through a second set of beaters 14 (substantially the same as the first set of beaters 12), which breaks them apart. The disaggregated coated seeds drop onto a conveyor 17 and cool to near ambient temperature as they are being transported to a storage container. The starch coating ranges from about 5% to about 7% of the weight of the dried, coated cottonseed.

EXAMPLE 2

Preparation of 1000 Kg of Coated Cottonseed with the Coating Containing a Nutritional Supplement The coated cotton seed is prepared as in Example 1 except that just before transfer from the cooker to the storage tank, 25 Kg of protected amino acid feed supplement and 0.5 Kg of USDA approved blue food coloring is blended into the gelatinous starch suspension. The coated cottonseed product is nutritionally enhanced and is colored blue so that it can be identified as such. Alternatively, the dry supplement and coloring are added at the point of starch application without pre-mixing.

EXAMPLE 3

Preparation of 1000 Kg Batch of Multiple Coated Cottonseed

The coated cottonseed is prepared in a similar manner as in Example 1 except that 600 L (rather than 450 L) of water is used to prepare the gelatinous starch suspension. This variation yields a thinner suspension. Further, the rate of application of the suspension is adjusted so that about one third of the batch of the suspension is placed on the 1000 Kg of cottonseed. After all the cottonseed has been coated and dried, it is returned to the seed hopper and coated and dried again. The coating process is repeated again to yield cottonseed bearing three thin coats of starch. This batch of coated cottonseed may also be used as planting stock.

EXAMPLE 4

Preparation of 1000 Kg Batch of Roasted and Heat-Steeped Coated Cottonseed

Referring to FIG. 2 and FIG. 3, a batch of coated cottonseed is prepared as in Example 1. However, rather than placing the coated cottonseed into storage as it leaves the second set of beaters 14, the coated cottonseed is allowed to fall onto a ventilated conveyor belt and enters a second conveyor drying chamber 15, substantially the same as conveyor drying chamber 10 (see FIG. 3). Here the coated cottonseed is heated by forced hot air (about 146° C.) during its transit time of about ten minutes. This heating further removes moisture from within the coated cottonseed and raises the internal temperature of the seeds to about 146° C. Upon leaving the drying chamber 15 the coated cottonseed passes into an insulated bin 16 to heat-steep for about 20 min before being cooled to ambient temperature and transferred to storage. The moisture content of coated cottonseed ranges from about 2% to about 4%.

We claim:

1. A process for preparing starch coated cottonseed consisting essentially of the following steps:

a) spraying linter-bearing cottonseed with a coating consisting essentially of a hot, aqueous, gelatinized starch suspension, optionally containing one or more biologically related materials selected from vitamins, feed supplements, oils, fats, urea, anti-fungal agents, rodent repellants, insect repellants, medications, anti-germination agents, and preservatives, while agitating said linter-bearing cottonseed to yield starch suspension coated cottonseed;

b) drying said starch suspension coated cottonseed to yield starch coated cottonseed;

c) disaggregating said starch coated cottonseed; and d) cooling and storing said starch coated cottonseed.

2. The process of claim 1 wherein steps a, b, and c are repeated one or more times.

3. The process of claim 1 wherein said starch coated cottonseed is roasted and heat-steeped after step c.

4. The process of claim 1 wherein said hot, aqueous gelatinized starch suspension is about 2% to about 25% starch by weight.

5. The process of claim 1 wherein said starch is corn starch.

6. The process of claim 1 wherein said hot, aqueous gelatinized starch suspension has been prepared by heating an aqueous suspension of corn starch, about 2% to about 25% by weight, to the boiling point until said suspension of corn starch has gelatinized.

7. Linter-bearing cottonseed covered with a coat consisting essentially of starch, applied as a hot, aqueous, gelatinized suspension, optionally containing one or more biologically related materials selected from, vitamins, feed supplements, oils, fats, urea, anti-fungal agents, rodent repellants, insect repellants, medications, anti-germination agents, and preservatives.

8. The linter-bearing cottonseed of claim 7 wherein said starch is corn starch.

9. The linter-bearing cottonseed of claim 7 wherein said coat of starch is about 5% to about 10% by weight on a dry basis.

10. The linter-bearing cottonseed of claim 7 wherein said coat of starch contains a coloring agent.

11. The linter-bearing cottonseed of claim 7 wherein said coat of starch contains vitamins and feed supplements.

12. An animal feed consisting essentially of linter-bearing cottonseed covered with a coat of starch, applied as a hot, aqueous, gelatinized suspension, optionally containing one or more biologically related materials selected from vitamins, feed supplements, oils, fats, urea, rodent repellants, insect repellants, medications, anti-germination agents, and preservatives.

13. Planting stock consisting essentially of linter-bearing cottonseed covered with a starch coat, applied as a hot, aqueous, gelatinized suspension, optionally containing one or more biologically related materials selected from anti-fungal agents, rodent repellants, insect repellants, germinating promoting agents, and preservatives.

* * * * *